United States Patent [19]

Katoh et al.

[11] Patent Number: 4,873,248
[45] Date of Patent: Oct. 10, 1989

[54] PYRIDINYLPYRIMIDINES HAVING FUNGICIDAL ACTIVITY

[75] Inventors: Tsuguhiro Katoh, Osaka; Kiyoto Maeda; Masao Shiroshita, both of Hyogo; Norihisa Yamashita, Osaka; Yuzuru Sanemitsu; Satoru Inoue, both of Hyogo, all of Japan

[73] Assignee: Sumitomo Chemical Co., Ltd., Osaka, Japan

[21] Appl. No.: 128,654

[22] Filed: Dec. 3, 1987

[30] Foreign Application Priority Data

Dec. 3, 1986 [JP] Japan ................ 61-288350

[51] Int. Cl.[4] .............. A61K 31/44; A61K 31/505; A01N 43/54; C07D 239/26; C07D 239/34
[52] U.S. Cl. ......................... 514/269; 71/92; 544/319; 544/333
[58] Field of Search .............. 544/319, 333; 514/269; 71/92

[56] References Cited

U.S. PATENT DOCUMENTS

| | | | |
|---|---|---|---|
| 3,944,581 | 3/1976 | Schwan | 544/333 |
| 4,032,523 | 6/1977 | Lesher et al. | 544/333 |
| 4,752,608 | 6/1988 | Katoh et al. | 544/333 |

FOREIGN PATENT DOCUMENTS

| | | | |
|---|---|---|---|
| 259139 | 3/1988 | European Pat. Off. | 544/333 |
| 11708 | 3/1974 | Japan | 544/333 |
| 11709 | 3/1974 | Japan | 544/333 |

OTHER PUBLICATIONS

W. Fife, "Cyanation in the Pyridine Series . . . Reactions", HETEROCYCLES, vol. 22, No. 10, 1984, pp. 2375-2394.

W. Fife, "Regioselective Cyanation of Pyridine . . . Reaction", J. ORG. CHEM., 1983, 48, pp. 1375-1377.

J. Lafferty, "The Preparation and Properties of Certain Pyridylpyrimidines . . . Iron(II)[1]", J. ORG. CHEM., 1967, 32, pp. 1591-1595.

S. Tseng, "A Simple Regioselective Synthesis of Pyrimido[1,2-a]benzimidazoles", J. HETEROCYCLIC CHEM., 1987, 24, pp. 837-843.

D. Brown, "Unfused Heterobicyles as . . . Thiazolylpyridines", Aust. J. Chem., 1980, 33, pp. 2291-2298.

D. Brown, "Unfused Heterobicyles as Amplifiers . . . Chains", Aust. J. Chem., 1982, 35, pp. 1203-1207.

*Primary Examiner*—Cecilia Shen
*Attorney, Agent, or Firm*—Sughrue, Mion, Zinn, Macpeak & Seas

[57] ABSTRACT

A novel pyridinylpyrimidine derivative of the formula below, a method for preparation thereof and a fungicide containing it,

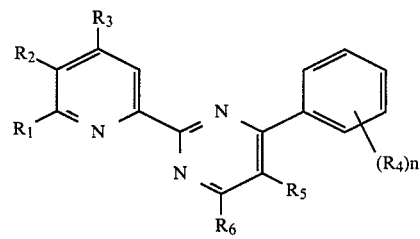

which is effective as a fungicide.

11 Claims, No Drawings

PYRIDINYLPYRIMIDINES HAVING FUNGICIDAL ACTIVITY

This invention relates to a novel pyridinylpyrimidine derivative, a method for preparation thereof and a fungicide containing it as an active ingredient.

The pyridinylpyrimidine derivatives such as 4-methyl-2-(2-pyridinyl)pyrimidine, 4-phenyl-2-(2-pyridinyl)-pyrimidine (J. Org. Chem. 32, 1591, (1967)) and N,N-dimethyl-2-(6-methyl-2-pyridylpyrimidine-4-ylthio)-ethyl amine (Aust. J. Chem., 35 1203 (1982)) are known.

However, it is not known at all that the pyridinylpyrimidine derivatives have fungicidal effect.

An object of the present invention is to provide a compound having preventive and curative controlling effects against many plant diseases.

The present inventors have found that pyridinylpyrimidine derivatives having the formula (I) mentioned below or their salts (hereinafter referred simply to as the present compound) have excellent fungicidal activity:

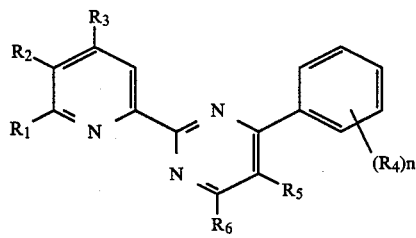
(I)

wherein $R_1$ is lower alkyl such as $C_1$-$C_4$ alkyl, $R_2$ and $R_3$ are, the same or different, each hydrogen or methyl, $R_4$ is, the same or different, each lower alkyl such as $C_1$-$C_3$ alkyl, lower alkoxy such as $C_1$-$C_3$ alkoxy, or halo(lower)alkyl whose alkyl is such as $C_1$-$C_3$ alkyl, or halogen; n is an integer of 0 to 5; $R_5$ is hydrogen, lower alkyl such as $C_1$-$C_3$ alkyl and $R_6$ is hydrogen, lower alkyl such as $C_1$-$C_3$ alkyl, lower alkoxy such as $C_1$-$C_3$ alkoxy, lower alkenyloxy such as $C_3$-$C_4$ alkenyloxy, or lower alkylthio whose alkyl is such as $C_1$-$C_3$ alkyl. Preferably, $R_1$ is lower alkyl such as $C_1$-$C_3$ alkyl, $R_2$ and $R_3$ are, the same or different, each hydrogen or methyl, $R_4$ is, the same or different, each lower alkyl such as methyl and ethyl, lower alkoxy such as methoxy and ethoxy, or halogen; n is an integer of 0 to 3, $R_5$ is hydrogen or methyl and $R_6$ is hydrogen, lower alkyl such as methyl and ethyl, lower alkoxy such as methoxy and ethoxy, or lower alkylthio such as methylthio. More preferably, $R_1$ is methyl, $R_2$ and $R_3$ are, the same or different, each hydrogen or methyl, $R_4$ is, the same or different, each methyl, methoxy, fluorine, chlorine or bromine, n is 0, 1 or 2; $R_5$ is hydrogen and $R_6$ is hydrogen, methyl or methoxy.

Plant diseases that can be controlled by the present compound include the followings:

Rice: *Pyricularia oryzae, Cochliobolus miyabeanus,* and *Rhizoctonia solani;*

Barley and wheat: *Erysiphe graminis* f. sp. *hordei, E. graminis* f. sp. *tritici, Pyrenophora graminea, Puccinia striiformis, P. graminis, P. recondita, P. hordei, Pseudocercosporella herpotrichoides, Rhynchosporium secalis, Septoria tritici,* and *Leptosphaeria nodorum;*

Citrus: *Diaporthe citri* and *Elsinoe fawcetti;*

Apple: *Podosphaera leucotricha, Alternaria mali,* and *Venturia inaequalis;*

Pear: *Venturia nashicola* and *Alternaria kikuchiana;*

Peach: *Sclerotinia cinerea;*

Grape: *Elsinoe ampelina, Glomerella cingulata* and *Uncinula necator;*

Melon crops: *Colletotrichum lagenarium* and *Sphaerotheca fuliginea;*

Tomato: *Alternaria solani* and *Phytophthora infestans;*

Eggplant: *Phomopsis vexans;*

Rape: *Alternaria japonica* and *Cercosporella brassicae;*

Welsh onion: *Puccinia allii;*

Soybean: *Cercospora kikuchii, Elsinoe glycines;*

Kidney bean: *Colletotrichum lindemuthianum;*

Peanut: *Mycosphaerella personatum* and *Cercospora arachidicola;*

Pea: *Erysiphe pisi;*

Potato: *Alternaria solani;*

Sugar beet: *Cercospora beticola;*

Rose: *Diplocarpon rosae* and *Sphaerotheca pannosa;*

Crop plants: *Botrytis cinerea* and *Sclerotinia sclerotiorum.*

Diseases more controllable among the above are Rice: *Pyricularia oryzae, Rhizoctonia solani,*

Barley and wheat: Septoria tritici, Pseudocercosporella herpotrichoides, and most controllable is *Pyricularia oryzae* against rice, *Septoria tritici, Pseudocercosporella herpotrichoides* against barley and wheat.

The pyridinylpyrimidine derivative (I) is typically prepared by the methods as shown below:

Procedure (a)

A pyridinylpyrimidine derivative of the formula:

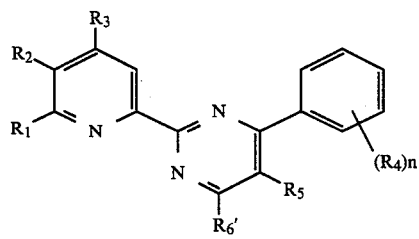
(II)

wherein $R_1$, $R_2$, $R_3$, $R_4$, $R_5$ and n are each defined as above and $R_6'$ is hydrogen is obtained by reductive dehalogenation of a halopyrimidine derivative of the formula:

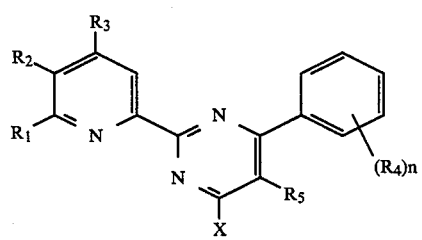
(III)

wherein $R_1$, $R_2$, $R_3$, $R_4$, $R_5$ and n are each defined as above and X is halogen.

The dehalogenation is, for example, carried out, in the presence of a catalyst such as palladium carbon, etc. under hydrogen gas in an inert solvent such as water, lower alcohol (e.g. methanol, ethanol, etc.), ethylacetate, toluene or a mixture thereof.

In this procedure, it is preferable to use of hydrogen gas having a pressure of a range from 1 to 3 atom.

In the procedure, it may be conducted in the presence of a dehydrohalogenating agent, such as a base (e.g., ammonia, sodium hydroxide, sodium carbonate, sodium acetate) or basic ion exchange resin (e.g., "Dowex" ® (a product of Dow Chemical Co.)).

The reaction may be carried out at room temperature to 50° C. for 0.5-3 hours.

After the reaction, the reaction mixture is filtered to remove the waste catalyst, and the filtrate is concentrated in vacuo to give a residue. When no dehydrohalogenating agent is used, aqueous solution of an inorganic base is added to the residue and the mixture is extracted with an organic solvent, while, when the dehydrohalogenating agent is used, water is added to the residue and the mixture is extracted with an organic solvent.

Then, the extract obtained above is treated in a usual manner such as concentration and further, if necessary, chromatography.

Procedure (b)

A pyridinylpyrimidine derivative of the formula:

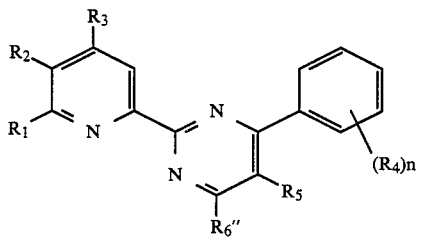

(IV)

wherein $R_1$, $R_2$, $R_3$, $R_4$, $R_5$ and n are each defined as above and $R_6''$ is lower alkoxy, lower alkenyloxy, or lower alkylthio, is obtained by allowing the halopyrimidine derivative (III) to react with an alkali methal compound of the formula

$R_6''Y$ (V)

wherein $R_6''$ is defined above and Y is an alkali metal atom. Examples of the alkali metal are a sodium atom, a potassium atom, etc.

The reaction may be carried out at 10°-120° C. for 1 to 48 hours.

The alkali metal compound (V) is usually used in amounts of about 1 to 1.5 equivalents to 1 equivalent of the halopyrimidine derivative (IV).

The reaction is usually carried out in the presence of a solvent such as an alcohol, an ether and a mixture thereof.

In case of using the alkali matal compound wherein $R_6''$ is lower alkoxy or lower alkenyloxy, the corresponding alcohol to $R_6''$ moiety (e.g. methanol, ethanol, allylalcohol, etc.), ether (e.g. diethyl ether, dioxane, tetrahydrofuran, etc.) or a mixture thereof is used as the solvent. In case of using the alkali metal compound wherein $R_6''$ is lower alkylthio, ether (e.g., diethylether, dioxane, tetrahydrofuran, etc.), nitrile (e.g. acetonitrile, etc.), aromatic hydrocarbon (e.g. toluene, etc.), water or a mixture thereof is used as the solvent.

After the reaction, the reaction mixture is concentrated in vacuo to obtain a residue. Then, the residue is subjected to a usual post-treatment such as extraction with organic solvent, concentration, and, if necessary, chromatography to obtain the objective compound (IV).

Procedure (c)

A pyridinylpyrimidine derivative of the formula:

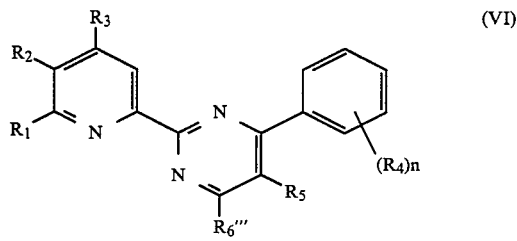

(VI)

wherein $R_1$, $R_2$, $R_3$, $R_4$, $R_5$ and n are each defined as above and $R_6'''$ is lower alkyl, is obtained by allowing the halopyrimidine derivative (III), in the presence of a base, to react with a diester derivative of the formula:

$R_7CH(COOR_8)_2$ (VII)

wherein $R_7$ is hydrogen, methyl or ethyl and $R_8$ is lower alkyl, followed by hydrolysis and decarbonation.

Examples of the base are alkali metal hydride (e.g. sodium hydride, etc.), alkyl lithium (e.g. n-butyl lithium, etc.), lithium dialkylamide (e.g. lithium diisopropylamide (LDA), etc.) and alkali metal hydroxide (e.g. sodium hydroxide, etc.).

The reaction may be carried out at 0°-150° C. for 0.5-24 hours.

The diester derivative (VII) and the base are usually used in amounts of 1 to 2 equivalents, respectively, to 1 equivalent of the halopyrimidine derivative (III).

The reaction is usually carried out in the presence of an inert solvent (e.g. nitriles such as acetonitrile, etc.; ethers such as diethylether, tetrahydrofuran, etc.; halohydrocarbons such as chloroform, etc.; aromatic hydrocarbons such as benzene, toluene, etc.; haloaromatic hydrocarbons such as chlorobenzene, etc.; ketones such as acetone, methylisobutyl ketone, etc.; esters such as ethylacetate, etc.; sulfur compounds such as dimethylsulfoxide and sulfolane, or mixture thereof, etc.).

After the reaction, the reaction mixture is subjected to a hydrolysis reaction and a decarbonation reaction to obtain the pyridinylpyrimidine derivative (VI). The hydrolysis and the decarbonation are typically carried out in the manner as shown below.

To the reaction mixture is added amounts of 2.1 to 5 equivalents of the base to 1 equivalent of the halopyrimidine derivative (III) in the form of an aqueous solution or an aqueous lower alcohol (e.g. methanol, ethanol) solution at 10°-100° C. for a period from 10 minutes to 24 hours. Examples of the base are alkali metal hydroxide (e.g. sodium hydroxide) and alkali metal carbonate (e.g. sodium carbonate).

To the reaction mixture obtained above is added amounts of 2.5 to 6 equivalents of acid to 1 equivalent of the used halopyrimidine derivative (III) for the decarbonation reaction. The decarbonation reaction may be carried out at 20°-150° C. for a period from 10 minutes to 24 hours.

Examples of the acid are inorganic acid such as sulfuric acid, hydrochloric acid, etc. and organic acid such as acetic acid, etc.

After the reaction, the reaction mixture is firstly neutralized with alkali metal hydroxide such as sodium hydroxide, etc., alkaline earth metal hydroxide such as calcium hydroxide, etc., alkali metal carbonate such as sodium carbonate, sodium bicarbonate, etc., or organic base such as triethylamine, etc.

Then, the reaction mixture is treated in a usual manner such as concentration and extraction, if necessary, recrystallization and column chromatography to obtain the pyridinylpyrimidine derivative (VI).

Procedure (d)

A pyridinylpyrimidine derivative of the formula:

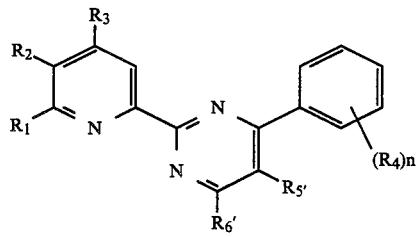
(VIII)

wherein $R_1$, $R_2$, $R_3$, $R_4$ and n are each defined as above and $R_5'$ and $R_6'$ are hydrogen, is obtained by allowing the picoline amidine derivative of the formula:

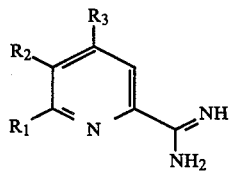
(IX)

wherein $R_1$, $R_2$ and $R_3$ are each defined as above, or its salt, in the presence of a base, to react with an enamine derivative of the formula:

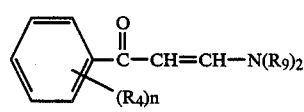
(X)

wherein $R_4$ and n are defined as above, and $R_9$ is lower alkyl.

Examples of the salt of picoline amidine derivative are hydrochloride, hydrobromide, acetate and formate. Examples of such base are alkali metal alkoxide such as sodium methoxide and sodium ethoxide and organic base such as triethylamine and N,N-diethylaniline. Sodium methoxide or sodium ethoxide is preferable.

The reaction is usually carried out in the presence of an inert solvent such as lower alcohol (e.g. methanol and ethanol), cyclic ether (e.g. dioxane and tetrahydrofuran), pyridine and N,N-dimethylformamide. The reaction may be carried out at 50°-150° C. for 1-6 hours.

The enamine derivative (X) and the base may be used in amounts of about 1 to 1.5 equivalents and about catalytic amount to 2.5 equivalents, respectively, to 1 equivalent of the picoline amidine derivative (IX) or its salt.

After the reaction, the reaction mixture is treated in an usual manner, such as concentration under reduced pressure, if necessary, chromatography to obtain the pyridinylpyrimidine derivative (VIII).

The present compound having the formula (I) is easily able to convert to salts thereof by allowing the compound to react with strong acid such as hydrochloric acid, hydrobromic acid, sulfuric acid or nitric acid.

The salt is typically obtained by the procedures shown below. The compound of the formula (I) is dissolved in a solvent and then one equivalent of the acid in the form of gas or aqueous solution is added thereto under ice cooling or at room temperature. After being left to stand for 10 minutes to one hours, the solution is subjected to post-treatment such as concentration under reduced pressure, and if necessary recrystallization. Examples of the solvent are lower alcohol such as methanol, ethanol, etc.; aromatic hydrocarbon such as toluene, benzene, etc.; ether such as ethyl ether, tetrahydrofuran, dioxane, etc.; halogenated hydrocarbon such as chloroform, etc.; ketone such as acetone, etc.; ester such as ethyl acetate, etc.; hydrocarbon such as hexane, etc.; water or a mixture thereof.

Picoline amidine derivative of the formula (IX) and halopyrimidine derivative of the formula (III) are typically prepared by the following reaction scheme:

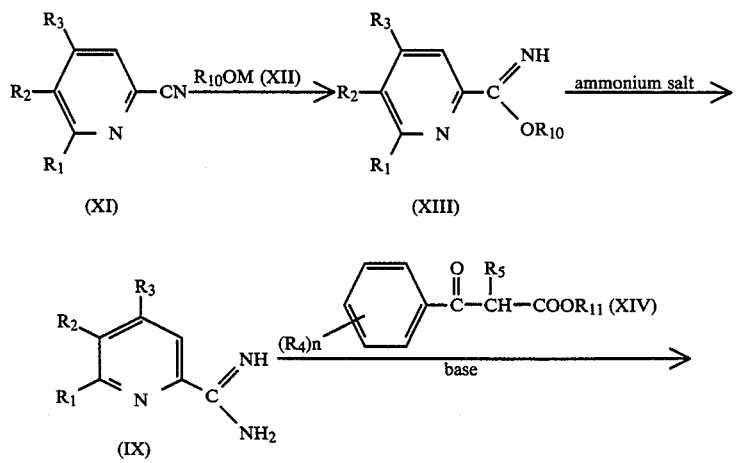

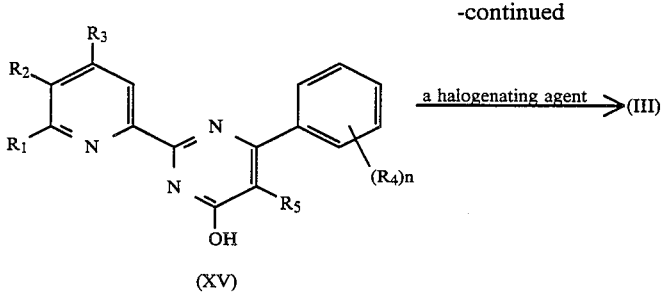

(XV)

wherein $R_1$, $R_2$, $R_3$, $R_4$, $R_5$ and n are each defined above, both $R_{10}$ and $R_{11}$ are lower alkyl and M is alkali metal atom.

An imidate derivative of the formula (XIII) is prepared by allowing a cyanopyridine derivative of the formula (XI), which is prepared by a method described in J. Org. Chem., 48, 1375-1377 (1983), to react with an alkoxide of the formula (XII). The picoline amidine of the formula (IX) is prepared by allowing the imidate derivative of the formula (XIII) to react with an ammonium salt, followed by the decomposition of a salt of the amidine derivative of the formula (IX) obtained. A hydroxypyrimidine derivative of the formula (XV) is obtained by allowing the picoline amidine derivative of the formula (IX) or a salt thereof, in the presence of a base, to react with a β-oxocarboxylate of the formula (XIV). The halopyrimidine derivative of the formula (III) is obtained by allowing the hydroxypyrimidine derivative of the formula (XV) to react with a halogenating agent.

Details of the above production are as follows.

A reaction between the compound of the formula (XI) and the compound of the formula (XII)

Examples of alkali metal atom in the alkoxide (XII) are a sodium atom, a potassium atom, etc. The reaction is usually carried out in the presence of a solvent at 10° to 50° C. for 1 to 48 hours. The alkoxide (XII) may be used in an amount of 0.1 to 1 equivalent to 1 equivalent of the cyanopyridine derivative (XI). As the solvent, there may be used, for example, a lower alcohol corresponding to $R_{10}$ of the alkoxide (XII), (e.g. methyl alcohol, ethyl alcohol, n-propyl alcohol, isopropyl alcohol, n-butyl alcohol, etc.), preferably methyl alcohol or ethyl alcohol.

After the reaction, neutralization of the solution is effected with acid, concentrated under reduced pressure and dissolved in an organic solvent. After insoluble alkali metal salt is filtered out, the filtrate is concentrated in vacuo, and, if necessary, distilled to obtain the imidate derivative (XIII).

A reaction between the compound (XIII) and ammonium salt

In the step, ammonium salt used is that of, for example, hydrochloric acid, hydrobromic acid, acetic acid or formic acid.

The reaction is usually carried out in the presence of a solvent at 30°-100° C. for 0.5-5 hours. The ammonium salt may be used in amounts of 1 to 1.1 equivalents to 1 equivalent of the imidate derivative (XIII). As the solvent, there may be used, for instance, a lower alcohol, preferably a solution of ethanol or water.

After the reaction, the reaction mixture may be concentrated in vacuo and, if necessary recrystallized to obtain such salt as hydrochloride, hydrobromide, acetate or formate of picoline amidine derivative of the formula (IX). The salt is decomposed by the usual manner such as neutralization with an inorganic base, for example, sodium hydroxide, potassium hydroxide, sodium methoxide, sodium ethoxide, etc. to obtain picoline amidine derivative of the formula (IX).

Alternatively, the salt may be subjected, as it is, to the next step where decomposition thereof is effected.

Reaction between picoline amidine derivative having the formula (IX) or its salt and the β-oxocarboxylate having the formula (XIV)

The reaction is usually carried out in the presence of a solvent at 50°-150° C. for 1-24 hours. The β-oxocarboxylate (XIV) may be used in amounts of 1 to 1.5 equivalents to 1 equivalent of the picoline amidine derivative (IX) or its salt. The base may be used from a catalytic amount to 1.5 equivalents to 1 equivalent of the picoline amidine derivative (IX) or its salt.

As the solvent, there may be used, for instance, lower alcohol such as methanol or ethanol, cyclic ether such as dioxane, tetrahydrofuran, pyridine, N,N-dimethylformamide, water or a mixture thereof.

As the base, there may be used, for instance, inorganic base such as sodium hydroxide, potassium hydroxide, potassium carbonate, or organic one such as alkali metal alkoxide such as sodium methoxide, triethylamine, N,N-diethylaniline, etc. After the reaction, in case of using the salt of picoline amidine derivative of the formula (IX), the by-produced inorganic salt is filtered out, and the filtrate is concentrated in vacuo to obtain a residue. The residue may be treated with chromatography or recrystallization to obtain the hydroxypyrimidine derivative (XV).

Reaction between the hydroxypyrimidine derivative having the formula (XV) and the halogenating agent As the halogenating agent, there may be used, for instance, thionyl chloride, phosgene, phosphoryl chloride, phosphorus pentachloride, phosphoryl bromide or phosphorus tribromide.

The reaction is usually carried out in the presence of a solvent at 50°-150° C. for 1-10 hours. The halogenating agent may be used in amounts of 1 to 10 equivalents to 1 equivalent of the hydroxypyrimidine derivative (XV). As the solvent, there may be used, for instance, aromatic hydrocarbons (e.g. benzene, toluene), halogenated hydrocarbons (e.g. chlorobenzene), etc.

After the reaction, post-treatment of the reaction mixture may be carried out in a usual manner. For instance, the reaction mixture is concentrated under reduced pressure and neutralized with an inorganic base (e.g. sodium hydroxide, etc.). Then, the above mixture is extracted with an organic solvent and the extract is concentrated in vacuo to obtain the halopyrimidine derivative (III). Any further procedure such as chromatography or recrystallization may be applied, if necessary, to the resultant product.

The pyridinyl pyrimidine derivatives of this invention may be used as an active ingredient of a fungicide, and it is usually mixed with a solid carrier, a liquid carrier, a surface active agent, and other adjuvants and formulated into emulsion, wettable powder, suspension, granule, dust, or liquid.

These formulations may contain the pyridinylpyrimidine derivative in a concentration of about 0.1 to 99% by weight, preferably about 0.2 to 95% by weight.

Examples of solid carriers include kaolin clay, attapulgite clay, bentonite, Japanese acid clay, pyrophyllite, talc, diatomaceous earth, calcite, corncob powder, walnut shell powder, urea, ammonium sulfate, and synthetic hydrated silica, which are in the form of finely divided powder or granule, etc. Examples of liquid carrier include aromatic hydrocarbons, e.g., xylene and methylnaphthalene; alcohols, e.g., isopropanol, ethylene glycol, and cellosolve; ketones, e.g., acetone, cyclohexanone, and isophorone; vegetable oils e.g., soybean oil and cottonseed oil; dimethylsulfoxide, acetonitrile, water, etc.

Examples of surface active agents for emulsification, dispersion, and wetting include anionic surface active agents such as alkyl sulfate salt, alkyl or aryl sulfonate, dialkylsulfosuccinate, polyoxyethylene alkylarylether phosphate salt, and naphthalene sulfonic acid-formalin condensate; and nonionic surface active agents such as polyoxyethylene alkyl ether, polyoxyethylene-polyoxypropylene block copolymer, sorbitan-fatty acid ester, polyoxyethylene-sorbitan fatty acid ester, etc. Examples of adjuvants include ligninsulfonate, alginate, polyvinyl alcohol, gum arabic, CMC (carboxymethylcellulose), PAP (isopropyl acidphosphate), etc.

These formulations are used as such or after dilution with water for foliage application or soil treatment or soil incorporation. They may also be used in combination with other plant disease protectants for their enhanced control effect.

Further, they may be used in combination with an insecticide, acaricide, nematicide, herbicide, plant growth regulator, fertilizer, and soil conditioner.

In the case where the present compound is used as an active ingredient of a plant disease protectant, the dosage varies depending on the weather conditions, formulation, application time, application method, application place, object diseases, and object crops. The dosage is usually 0.2 to 200 g, preferably 1 to 100 g for an area of 1 are. In the case of emulsion, wettable powder, suspension, or liquid formulation which is diluted with water prior to application, the concentration should be 0.005 to 0.5%, preferably 0.01 to 0.2% by weight. Granules and dusts are used as such without dilution.

The present invention is explained in further detail referring to synthesis examples, formulation examples and efficiency tests.

Synthesis examples of the present compound

EXAMPLE 1

To a solution of 4-chloro-2-(6-methyl-2-pyridinyl)-6-o-tolylpyrimidine (1 g) in toluene (10 ml) and ethanol (5 ml), were added a sodium carbonate (0.27 g) solution in water (5 ml) and then 5% palladium carbon (0.1 g).

The mixture was brought into contact with hydrogen gas for 30 minutes. After palladium carbon was filtered off, water (20 ml) was added and then extracted with toluene (30 ml). After the extract was dried over anhydrous magnesium sulfate, it was concentrated under reduced pressure to obtain 2-(6-methyl-2-pyridinyl)-6-o-tolylpyrimidine (0.81 g).

m.p. 119.4° C.
PMR (CDCl$_3$) δppm:
2.53 (s, 3H, —C$\underline{H_3}$)
2.74 (s, 3H, —C$\underline{H_3}$)
9.00 (d, 1H, pyrimidine-H$^6$, J=4.2 Hz).

EXAMPLE 2

To the mixture of 4-chloro-6-o-fluoro phenyl-2-(6-metyl-2-pyridinyl)pyrimidine (1 g) was added sodium methoxide prepared from methanol (10 ml) and metallic sodium (0.1 g). After the mixture was left to stand at room temperature for 1 hour, water (30 ml) and ethyl acetate (100 ml) were added thereto, and then extracted. After the extract was dried over anhydrous magnesium sulfate, it was concentrated under reduced pressure to obtain 4-o-fluorophenyl-6-methoxy-2-(6-methyl-2-pyridinyl)pyrimidine (0.82 g).

m.p. 99.5° C.
PMR (CDCl$_3$) δppm:
2.65 (s, 3H, —C$\underline{H_3}$)
4.08 (s, 3H, —OC$\underline{H_3}$)
7.58 (t, 1H, pyridine-H$^4$, J=7.2 Hz).

EXAMPLE 3

To tetrahydrofuran (30 ml) were added diethylmalonate (1.5 g) and 60% oily sodium hydride (0.4 g), and then 4-chloro-6-o-chlorophenyl-2-(6-methyl-2-pyridinyl)pyrimidine (2 g). The mixture was heated under reflux for 30 minutes. Sodium hydroxide (0.8 g) solution in water (10 ml) and methanol (10 ml) were added thereto, and the mixture was further heated under reflux for 20 minutes.

After the mixture was left to stand until it was cooled to room temperature, sulfuric acid (1.5 g) was added dropwise thereto. The mixture was heated under reflux for 30 minutes and left to stand to room temperature. 1-N aqueous sodium carbonate solution was added until a mixture was neutralized, and concentrated under reduced pressure. The residue was subjected to silica-gel column chromatography (eluent; n-hexane:acetone=3:1 in volume) to give 4-o-chlorophenyl-6-methyl-2-(6-methyl-2-pyridinyl)pyrimidine (1.42 g).

m.p. 90.8° C.
PMR (CDCl$_3$) δppm:
2.70 (s, 6H, —C$\underline{H_3}$×2)
8.31 (d, 1H, pyridine-H$^3$, J=7.8 Hz).

EXAMPLE 4

To the mixture of 6-methyl-2-picoline amidine hydrochloride (1.5 g) and methanol (50 ml) were added 28% sodium methoxide solution in methanol (2.2 g) and 3-dimethylamino-1-phenyl-2-butene-1-one (1.7 g). After the mixture was heated under reflux for 2 hours, it was concentrated under reduced pressure. The residue obtained was subjected to silica gel column chromatography (eluent; n-hexane:ethylacetate=2:1 in volume) to obtain 2-(6-methyl-2-pyridinyl)-4-phenylpyrimidine (1.6 g).

n$_D^{24}$ 1.6329.
PMR (CDCl$_3$) δppm:
2.74 (s, 3H, —C$\underline{H_3}$)
8.43 (d, 1H, pyridine-H$^3$, J=7.2 Hz)

8.92 (d, 1H, pyrimidine-H$^6$, J=6.0 Hz).

Some of compounds of this invention which are prepared according to the similar procedures to the above are listed in Table 1.

TABLE 1

Pyridinylpyrimidine derivatives or salts thereof

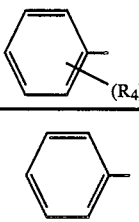

| Compound number | $R_1$ | $R_2$ | $R_3$ | $(R_4)_n$ | $R_5$ | $R_6$ | Physical constant |
|---|---|---|---|---|---|---|---|
| 1 | CH$_3$ | H | H |  | H | H | $n_D^{24}$ 1.6329 |
| 2 | CH$_3$ | H | H |  | H | OCH$_3$ | m.p. 107.7° C. |
| 3 | CH$_3$ | H | H | 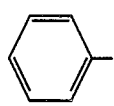 | H | OCH$_2$CH=CH$_2$ | $n_D^{22.5}$ 1.6140 |
| 4 | CH$_3$ | H | H | 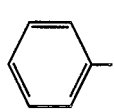 | H | n-C$_3$H$_7$ | m.p. 87.2° C. |
| 5 | CH$_3$ | H | H |  | H | H | m.p. 119.4° C. |
| 6 | CH$_3$ | H | H | 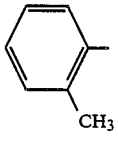 | H | OCH$_3$ | m.p. 96.7° C. |
| 7 | CH$_3$ | H | H | 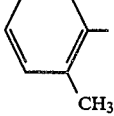 | H | CH$_3$ | m.p. 83.2° C. |
| 8 | CH$_3$ | H | H | 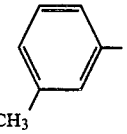 | CH$_3$ | H | $n_D^{22.5}$ 1.6170 |

TABLE 1-continued

Pyridinylpyrimidine derivatives or salts thereof

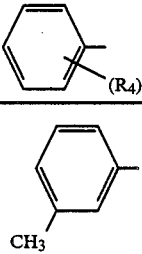

| Compound number | $R_1$ | $R_2$ | $R_3$ | $(R_4)_n$ aryl | $R_5$ | $R_6$ | Physical constant |
|---|---|---|---|---|---|---|---|
| 9 | $CH_3$ | H | H | 3-CH$_3$-phenyl | H | $OCH_3$ | $n_D^{26}$ 1.6990 |
| 10 | $CH_3$ | H | H | 3-CH$_3$-phenyl | H | $OC_2H_5$ | $n_D^{23}$ 1.6010 |
| 11 | $CH_3$ | H | H | 3-CH$_3$-phenyl | $CH_3$ | $OCH_3$ | m.p. 119.7° C. |
| 12 | $CH_3$ | H | H | 4-CH$_3$-phenyl | H | $OCH_3$ | m.p. 82.2° C. |
| 13 | $CH_3$ | H | H | 4-CH$_3$-phenyl | H | $OC_2H_5$ | m.p. 78.7° C. |
| 14 | $CH_3$ | H | H | 2,4-(CH$_3$)$_2$-phenyl | H | $OCH_3$ | m.p. 97.7° C. |
| 15 | $CH_3$ | H | H | 2,4-(CH$_3$)$_2$-phenyl | H | H | $n_D^{25}$ 1.6081 |
| 16 | $CH_3$ | H | H | 2,4,6-(CH$_3$)$_3$-phenyl | H | H | $n_D^{23.5}$ 1.5888 |

TABLE 1-continued

Pyridinylpyrimidine derivatives or salts thereof

| Compound number | $R_1$ | $R_2$ | $R_3$ | $(R_4)_n$ | $R_5$ | $R_6$ | Physical constant |
|---|---|---|---|---|---|---|---|
| 17 | $CH_3$ | H | H | 3-$C_2H_5$ | H | H | $n_D^{28}$ 1.5999 |
| 18 | $CH_3$ | H | H | 2-$CF_3$ | H | $OCH_3$ | m.p. 129.4° C. |
| 19 | $CH_3$ | H | H | 2-F | H | $OCH_3$ | m.p. 99.5° C. |
| 20 | $CH_3$ | H | H | 2-F | H | $OC_2H_5$ | m.p. 72.2° C. |
| 21 | $CH_3$ | $CH_3$ | H | 2-F | H | $OCH_3$ | m.p. 86.5° C. |
| 22 | $CH_3$ | H | $CH_3$ | 2-F | H | $OCH_3$ | m.p. 76.0° C. |
| 23 | $CH_3$ | H | H | 2-F | H | $CH_3$ | m.p. 71.5° C. |
| 24 | $CH_3$ | $CH_3$ | H | 2-F | H | H | m.p. 93.5° C. |

TABLE 1-continued

Pyridinylpyrimidine derivatives or salts thereof

| Compound number | $R_1$ | $R_2$ | $R_3$ | $(R_4)_n$ | $R_5$ | $R_6$ | Physical constant |
|---|---|---|---|---|---|---|---|
| 25 | $CH_3$ | H | $CH_3$ | 2-F-phenyl | H | H | m.p. 125.5° C. |
| 26 | $CH_3$ | $CH_3$ | H | 2-F-phenyl | H | $CH_3$ | m.p. 106.9° C. |
| 27 | $CH_3$ | H | H | 2,4-diF-phenyl | H | H | m.p. 131.2° C. |
| 28 | $CH_3$ | $CH_3$ | H | 2,4-diF-phenyl | H | H | m.p. 145.0° C. |
| 29 | $CH_3$ | H | $CH_3$ | 2,4-diF-phenyl | H | H | m.p. 121.2° C. |
| 30 | $CH_3$ | H | H | 2,6-diF-phenyl | H | $OCH_3$ | m.p. 108.9° C. |
| 31 | $CH_3$ | H | H | 2-Cl-phenyl | H | H | m.p. 86.0° C. |
| 32 | $CH_3$ | H | H | 2-Cl-phenyl | H | $OCH_3$ | $n_D^{21}$ 1.5878 |

TABLE 1-continued

Pyridinylpyrimidine derivatives or salts thereof

| Compound number | $R_1$ | $R_2$ | $R_3$ | $(R_4)_n$ | $R_5$ | $R_6$ | Physical constant |
|---|---|---|---|---|---|---|---|
| 33 | $CH_3$ | H | H | 2-Cl-phenyl | H | $OC_2H_5$ | $n_D^{24.5}$ 1.6055 |
| 34 | $CH_3$ | H | H | 2-Cl-phenyl | H | $CH_3$ | m.p. 90.8° C. |
| 35 | $CH_3$ | H | H | 3-Cl-phenyl | H | $OCH_3$ | m.p. 118.4° C. |
| 36 | $CH_3$ | H | H | 2-Br-phenyl | H | H | m.p. 120.6° C. |
| 37 | $CH_3$ | H | H | 3-Br-phenyl | H | H | $n_D^{24.5}$ 1.6186 |
| 38 | $CH_3$ | H | H | 2-$OCH_3$-phenyl | H | $OCH_3$ | Resin |
| 39 | $CH_3$ | H | H | 2-$OCH_3$-phenyl | H | $CH_3$ | m.p. 104.4° C. |
| 40 | $CH_3$ | H | H | 4-$CH_3O$-phenyl | H | H | m.p. 64.7° C. |

TABLE 1-continued

Pyridinylpyrimidine derivatives or salts thereof

| Compound number | R₁ | R₂ | R₃ | (R₄)ₙ phenyl substituents | R₅ | R₆ | Physical constant |
|---|---|---|---|---|---|---|---|
| 41 | CH₃ | H | H | 2,3-(CH₃O)₂, 6-CH₃ phenyl | H | H | $n_D^{22.5}$ 1.6021 |
| 42 | C₂H₅ | H | H | 3-CH₃ phenyl | H | H | $n_D^{22.5}$ 1.6269 |
| 43 | C₂H₅ | H | H | 2-Cl phenyl | H | OCH₃ | $n_D^{21}$ 1.5978 |
| 44 | n-C₃H₇ | H | H | phenyl | H | H | m.p. 61.7° C. |
| 45 | n-C₃H₇ | H | H | 2-Cl phenyl | H | OCH₃ | $n_D^{21}$ 1.5732 |
| 46 | CH₃ | H | H | phenyl | H | SCH₃ | m.p. 95.6° C. |
| 47 | CH₃ | H | H | 2,3,6-Cl₃ phenyl | H | H | m.p. 175.3° C. |
| 48 | iso-C₃H₇ | H | H | phenyl | H | H | $n_D^{23.5}$ 1.6192 |
| 49 | HCl salt of compound number 31 | | | | | | m.p. 167.3° C. |
| 50 | ½ H₂SO₄ salt of compound number 31 | | | | | | m.p. 93.8° C. |

The following reference examples show the preparation of various starting compounds.

Preparation of picoline amidine derivative (IX) (HCl-salt)

To the solution of 2-cyano-6-methylpyridine (30 g) and methanol (300 ml) was added 28% sodium methoxide solution in methanol (14.7 g). After the solution was left to stand for 3 hours, acetic acid (4.6 g) was added thereto, followed by concentration under reduced pressure. The resultant residue was dissolved in ether (300 ml) and washed with water (100 ml). After the extract was dried over anhydrous magnesium sulfate, it was concentrated under reduced pressure to obtain methyl 6-methyl-2-picoline imidate.

To the imidate obtained above was added a solution of ammonium chloride (13.6 g) in water (50 ml) and ethanol (200 ml), and the mixture was heated under reflux for 30 minutes. After being left to stand to cool, the reaction mixture was concentrated under reduced pressure. The crystalline residue was washed with acetone to obtain 6-methyl-2-picoline amidine hydrochloride (37 g).

m.p. 188.0° C.

Some of picoline amidine derivatives or salts thereof having the formula (IX) which are able to prepare according to the similar procedure to the above are listed in Table 2.

TABLE 2

Picoline amidine derivatives or their salts

| $R_1$ | $R_2$ | $R_3$ | Physical constant |
|---|---|---|---|
| $CH_3$ | H | H | m.p. 188.0° C. (HCl-salt) |
| $CH_3$ | $CH_3$ | H | m.p. 263.0° C. (HCl-salt) |
| $CH_3$ | H | $CH_3$ | m.p. 273.0° C. (HCl-salt) |
| $C_2H_5$ | H | H | m.p. 171.8° C. (HCl-salt) |
| n-$C_3H_7$ | H | H | m.p. 173.0° C. (HCl-salt) |

REFERENCE EXAMPLE 2

Preparation of hydroxypyrimidine derivative (XV)

6-Methyl-2-picoline amidine hydrochloride (5 g) was dissolved in a solution of sodium methoxide in ethanol prepared from ethanol (50 ml) and metallic sodium (0.8 g). Ethyl o-chlorobenzoyl acetate (7.3 g) was added to the solution obtained above, then the mixture was heated uner reflux for 1 hour. After the reaction mixture was cooled to room temperature, it was neutralized with acetic acid and then concentrated under reduced pressure. The residue obtained was washed with water and n-hexane to obtain 4-o-chlorophenyl-6-hydroxy-2-(6-methyl-2-pyridinyl)pyrimidine (7 g).

m.p. 196.0° C.

PMR (CDCl$_3$) δppm:
2.65 (s, 3H, —CH$_3$)
6.66 (s, 1H, pyrimidine-H$^5$)
7.84 (t, 1H, pyridine-H$^4$, J=7.2 Hz)
8.23 (d, 1H, pyridine-H$^3$, J=7.2 Hz).

Some of hydroxypyrimidine derivatives (XV) prepared according to the similar procedure to the above are listed in Table 3.

TABLE 3

Hydroxypyrimidine derivatives

| $R_1$ | $R_2$ | $R_3$ | $(R_4)_n$ | $R_5$ | Physical constant |
|---|---|---|---|---|---|
| $CH_3$ | H | H | phenyl | H | m.p. 158.8° C. |
| $CH_3$ | H | H | 2-CH$_3$-phenyl | H | m.p. 140.6° C. |
| $CH_3$ | H | H | 3-CH$_3$-phenyl | H | m.p. 139.6° C. |
| $CH_3$ | H | H | 3-CH$_3$-phenyl | $CH_3$ | m.p. 151.7° C. |
| $CH_3$ | H | H | 4-CH$_3$-phenyl | H | m.p. 184.7° C. |
| $CH_3$ | H | H | 3,4-diCH$_3$-phenyl | H | m.p. 145.6° C. |
| $CH_3$ | H | H | 2-CF$_3$-phenyl | H | m.p. 159.6° C. |
| $CH_3$ | H | H | 2-Cl-phenyl | H | m.p. 196.0° C. |

TABLE 3-continued
Hydroxypyrimidine derivatives

| $R_1$ | $R_2$ | $R_3$ | (R4)n | $R_5$ | Physical constant |
|---|---|---|---|---|---|
| $CH_3$ | H | H | (phenyl, 2-F) | H | m.p. 188.0° C. |
| $CH_3$ | H | H | (phenyl, 2,3-diF) | H | m.p. 187.8° C. |
| $CH_3$ | H | H | (phenyl, 2-OCH3) | H | m.p. 199.3° C. |

REFERENCE EXAMPLE 3

Preparation of halopyrimidine derivative (III)

Phosphoryl chloride (5 g) was added to the solution of 4-o-chlorophenyl-6-hydroxy-2-(6-methyl-2-pyridinyl)pyrimidine (5 g) in toluene (100 ml). The mixture was heated under reflux for 1 hour and left to stand to room temperature. Aqueous sodium carbonate solution was added thereto until the reaction solution became about pH 8 to be separated into two layers. Toluene layer was washed with water and dried over anhydrous magnesium sulfate. The toluene layer was concentrated under reduced pressure to obtain 4-chloro-6-o-chlorophenyl-2-(6-methyl-2-pyridinyl)-pyrimidine (4.6 g).

m.p. 133.0° C.
PMR (CDCl$_3$) δppm:
2.63 (s, 3H, —CH$_3$)
8.18 (d, 1H, pyridine-H$^3$, J=7.2 Hz).

Some of halopyrimidine derivatives (III) prepared according to the similar procedure to the above are listed in Table 4.

TABLE 4
Halopyrimidine derivatives

| $R_1$ | $R_2$ | $R_3$ | (R4)n | $R_5$ | X | Physical constant |
|---|---|---|---|---|---|---|
| $CH_3$ | H | H | (phenyl, 2-CH3) | H | Cl | m.p. 100.3° C. |
| $CH_3$ | H | H | (phenyl, 3-CH3) | H | Cl | m.p. 128.8° C. |
| $CH_3$ | H | H | (phenyl, 3-CH3) | $CH_3$ | Cl | m.p. 110.1° C. |
| $CH_3$ | H | H | (phenyl, 4-CH3) | H | Cl | m.p. 136.9° C. |
| $CH_3$ | H | H | (phenyl, 2,5-diCH3) | H | Cl | m.p. 127.2° C. |
| $CH_3$ | H | H | (phenyl, 2-CF3) | H | Cl | m.p. 93.0° C. |
| $CH_3$ | H | H | (phenyl, 2-Cl) | H | Cl | m.p. 133.0° C. |
| $CH_3$ | H | H | (phenyl, 2-F) | H | Cl | m.p. 111.2° C. |

TABLE 4-continued

Halopyrimidine derivatives

[Structure: pyridine-pyrimidine derivative with R1, R2, R3 on pyridine ring; N-containing six-membered ring with phenyl group bearing (R4)n, R5, and X substituents]

| $R_1$ | $R_2$ | $R_3$ | (R4)n (phenyl) | $R_5$ | X | Physical constant |
|-------|-------|-------|----------------|-------|-----|-------------------|
| CH$_3$ | CH$_3$ | H | 2-F-phenyl | H | Cl | m.p. 134.4° C. |
| CH$_3$ | H | CH$_3$ | 2-F-phenyl | H | Cl | m.p. 112.4° C. |
| CH$_3$ | H | H | 2,6-diF-phenyl | H | Cl | m.p. 148.3° C. |
| CH$_3$ | H | H | 2-OCH$_3$-phenyl | H | Cl | m.p. 151.4° C. |

FORMULATION EXAMPLES

The present compounds used are identified by numbers shown in Table 1. Quantities are expressed by parts by weight.

FORMULATION EXAMPLE 1

A wettable powder each was prepared by mixing and pulverizing 50 parts of each of the present compounds (1)–(50), 3 parts of calcium ligninsulfonate, 2 parts of sodium lauryl sulfate, and 45 parts of synthetic hydrated silica.

FORMULATION EXAMPLE 2

A suspension each was prepared by mixing 25 parts of each of the present compounds (1)–(50), 3 parts of polyoxyethylene sorbitanmonooleate, 3 parts of CMC, and 69 parts of water, followed by wet grinding to give a particle size smaller than 5 microns.

FORMULATION EXAMPLE 3

A dust each was prepared by mixing and pulverizing 2 parts of each of the present compounds (1)–(56), 88 parts of kaolin clay, and 10 parts of talc.

FORMULATION EXAMPLE 4

An emulsifiable concentrate each was prepared by thoroughly mixing 20 parts of each of the present compounds (1)–(50), 14 parts of polyoxyethylene styrylphenyl ether, 6 parts of calcium dodecylbenzenesulfonate, and 60 parts of xylene.

FORMULATION EXAMPLE 5

A granule each was prepared by mixing and pulverizing 2 parts of each of the present compounds (1)–(50), 1 part of synthetic hydrated silica, 2 parts of calcium ligninsulfonate, 30 parts of bentonite, and 65 parts of kaolin clay, followed by kneading with water, granulation, and drying.

The following test examples demonstrate the effectiveness of the present compound used as an active ingredient of plant disease protectants. The present compounds used in the test examples are identified by the compound numbers shown in Table 1, and the compounds used for control are identified by the compound symbols shown in Table 5.

TABLE 5

| Compound symbol | Compound | Remarks |
|---|---|---|
| A | (iso C$_3$H$_7$O)$_2$P(=O)—SCH$_2$—phenyl | Commercial fungicide "IBP" |
| B | benzimidazole-2-NHCOCH$_3$ | Commercial fungicide "MBC" |
| C | tetrachloroisophthalonitrile (Cl$_4$-benzene-1,3-(CN)$_2$) | Commercial fungicide "TPN" |
| D | N-(1,1,2,2-tetrachloroethylthio)-4-cyclohexene-1,2-dicarboximide | Commercial fungicide "Captafol" |

The controlling effect was evaluated by visually observing the degree of fungus colony and infected area of on the leaves and stems of the test plants. The results of evaluation were expressed in terms of six ratings as follows:

"5" Not observed at all.
"4" Observed on about 10% of the leaves and stems.
"3" Observed on about 30% of the leaves and stems.
"2" Observed on about 50% of the leaves and stems.
"1" Observed on about 70% of the leaves and stems.
"0" Same as control.

TEST EXAMPLE 1

Test for preventive controlling effect on blast (*Pyricularia oryzae*) of rice

Rice seeds (var.: Kinki No. 33) were sown in the sandy loam filled in a plastic pot. After raising for 20 days in a greenhouse, the seedlings were subjected to foliage application with a spray liquid of the wettable powder prepared according to Formulation Example 1 which was diluted with water to the given concentrations. After application, the seedings were air-dried and then inoculated with spores of *Pyricularia oryzae* by spraying a suspension of spores. The inoculated seedlings were grown in a dark damp place at 28° C. for 4 days, and the controlling effect was examined. The results are shown in Table 6.

TABLE 6

| Compound No. | Concentration of active ingredient (ppm) | Control effect |
| --- | --- | --- |
| Present compound | | |
| (1) | 200 | 5 |
| | 100 | 5 |
| | 50 | 4 |
| (2) | 200 | 5 |
| | 100 | 5 |
| | 50 | 5 |
| (3) | 200 | 5 |
| | 100 | 5 |
| | 50 | 5 |
| (4) | 200 | 5 |
| | 100 | 5 |
| | 50 | 5 |
| (5) | 200 | 5 |
| | 100 | 5 |
| | 50 | 5 |
| (6) | 200 | 5 |
| | 100 | 5 |
| | 50 | 5 |
| (7) | 200 | 5 |
| | 100 | 5 |
| | 50 | 5 |
| (8) | 200 | 5 |
| | 100 | 5 |
| | 50 | 5 |
| (9) | 200 | 5 |
| | 100 | 5 |
| | 50 | 5 |
| (10) | 200 | 5 |
| | 100 | 5 |
| | 50 | 4 |
| (11) | 200 | 5 |
| | 100 | 5 |
| | 50 | 5 |
| (12) | 200 | 5 |
| | 100 | 5 |
| | 50 | 5 |
| (13) | 200 | 5 |
| | 100 | 5 |
| | 50 | 5 |
| (14) | 200 | 5 |
| | 100 | 5 |
| | 50 | 5 |
| (15) | 200 | 5 |
| | 100 | 5 |
| | 50 | 5 |
| (16) | 200 | 5 |
| | 100 | 5 |
| | 50 | 5 |
| (17) | 200 | 5 |
| | 100 | 5 |
| | 50 | 4 |
| (19) | 200 | 5 |
| | 100 | 5 |
| | 50 | 5 |
| (20) | 200 | 5 |
| | 100 | 5 |
| | 50 | 5 |

TABLE 6-continued

| Compound No. | Concentration of active ingredient (ppm) | Control effect |
| --- | --- | --- |
| (21) | 200 | 5 |
| | 100 | 5 |
| | 50 | 5 |
| (22) | 200 | 5 |
| | 100 | 5 |
| | 50 | 5 |
| (23) | 200 | 5 |
| | 100 | 5 |
| | 50 | 5 |
| (24) | 200 | 5 |
| | 100 | 5 |
| | 50 | 5 |
| (25) | 200 | 5 |
| | 100 | 5 |
| | 50 | 5 |
| (26) | 200 | 5 |
| | 100 | 5 |
| | 50 | 5 |
| (27) | 200 | 5 |
| | 100 | 5 |
| | 50 | 4 |
| (28) | 200 | 5 |
| | 100 | 5 |
| | 50 | 4 |
| (29) | 200 | 5 |
| | 100 | 5 |
| | 50 | 4 |
| (30) | 200 | 5 |
| | 100 | 5 |
| | 50 | 5 |
| (31) | 200 | 5 |
| | 100 | 5 |
| | 50 | 5 |
| (32) | 200 | 5 |
| | 100 | 5 |
| | 50 | 5 |
| (33) | 200 | 5 |
| | 100 | 5 |
| | 50 | 5 |
| (34) | 200 | 5 |
| | 100 | 5 |
| | 50 | 5 |
| (35) | 200 | 5 |
| | 100 | 5 |
| | 50 | 5 |
| (36) | 200 | 5 |
| | 100 | 5 |
| | 50 | 5 |
| (37) | 200 | 5 |
| | 100 | 5 |
| | 50 | 4 |
| (38) | 200 | 5 |
| | 100 | 5 |
| | 50 | 5 |
| (39) | 200 | 5 |
| | 100 | 5 |
| | 50 | 5 |
| (40) | 200 | 5 |
| | 100 | 5 |
| | 50 | 4 |
| (41) | 200 | 5 |
| | 100 | 5 |
| | 50 | 5 |
| (42) | 200 | 5 |
| | 100 | 5 |
| | 50 | 5 |
| (43) | 200 | 5 |
| | 100 | 5 |
| | 50 | 5 |
| (44) | 200 | 5 |
| | 100 | 5 |
| | 50 | 4 |
| (45) | 200 | 5 |
| | 100 | 5 |
| | 50 | 5 |
| (46) | 200 | 5 |
| | 100 | 5 |
| | 50 | 4 |
| (47) | 200 | 5 |
| | 100 | 5 |

TABLE 6-continued

| Compound No. | Concentration of active ingredient (ppm) | Control effect |
| --- | --- | --- |
| (48) | 50 | 5 |
|  | 200 | 5 |
|  | 100 | 5 |
| (49) | 50 | 5 |
|  | 200 | 5 |
|  | 100 | 5 |
| (50) | 50 | 5 |
|  | 200 | 5 |
|  | 100 | 5 |
| A | 50 | 5 |
|  | 200 | 4 |

TEST EXAMPLE 2

Test for curative controlling effect on blast (*Pyricularia oryzae*) or rice

Rice seeds (var.: Kinki No. 33) were sown in the sandy loam filled in a plastic pot. After raising for 20 days in a greenhouse, the seedlings were inoculated with spores of *Pyricularia oryzae* by spraying a suspension of spores. The inoculated seedlings were grown in a dark damp place at 28° C. for 16 hours. The seedlings were subjected to foliage application with a spray liquid of the emulsion prepared according to Formulation Example 4 which was diluted with water to the given concentrations. After application, the seedlings were grown in a dark damp place at 28° C. for 3 days, and the controlling effect was examined. The results are shown in Table 7.

TABLE 7

| Compound No. | Concentration of ingredient (ppm) | Control effect |
| --- | --- | --- |
| Present compound |  |  |
| (1) | 200 | 5 |
|  | 100 | 5 |
|  | 50 | 4 |
| (2) | 200 | 5 |
|  | 100 | 5 |
|  | 50 | 5 |
| (3) | 200 | 5 |
|  | 100 | 5 |
|  | 50 | 4 |
| (4) | 200 | 5 |
|  | 100 | 5 |
|  | 50 | 5 |
| (5) | 200 | 5 |
|  | 100 | 5 |
|  | 50 | 5 |
| (6) | 200 | 5 |
|  | 100 | 5 |
|  | 50 | 4 |
| (7) | 200 | 5 |
|  | 100 | 5 |
|  | 50 | 4 |
| (8) | 200 | 5 |
|  | 100 | 5 |
|  | 50 | 5 |
| (9) | 200 | 5 |
|  | 100 | 5 |
|  | 50 | 5 |
| (10) | 200 | 5 |
|  | 100 | 4 |
|  | 50 | 4 |
| (11) | 200 | 5 |
|  | 100 | 5 |
|  | 50 | 5 |
| (12) | 200 | 5 |
|  | 100 | 5 |
|  | 50 | 5 |
| (13) | 200 | 5 |
|  | 100 | 5 |

TABLE 7-continued

| Compound No. | Concentration of ingredient (ppm) | Control effect |
| --- | --- | --- |
|  | 50 | 5 |
| (14) | 200 | 5 |
|  | 100 | 5 |
| (15) | 50 | 5 |
|  | 200 | 5 |
|  | 100 | 5 |
| (16) | 50 | 5 |
|  | 200 | 5 |
|  | 100 | 5 |
| (17) | 50 | 5 |
|  | 200 | 5 |
|  | 100 | 5 |
| (19) | 50 | 4 |
|  | 200 | 5 |
|  | 100 | 5 |
| (20) | 50 | 5 |
|  | 200 | 5 |
|  | 100 | 5 |
| (21) | 50 | 5 |
|  | 200 | 5 |
|  | 100 | 5 |
| (22) | 50 | 5 |
|  | 200 | 5 |
|  | 100 | 4 |
| (23) | 50 | 4 |
|  | 200 | 5 |
|  | 100 | 5 |
| (24) | 50 | 5 |
|  | 200 | 5 |
|  | 100 | 5 |
| (25) | 50 | 4 |
|  | 200 | 5 |
|  | 100 | 4 |
| (26) | 50 | 4 |
|  | 200 | 5 |
|  | 100 | 5 |
| (27) | 50 | 5 |
|  | 200 | 5 |
|  | 100 | 5 |
| (28) | 50 | 5 |
|  | 200 | 5 |
|  | 100 | 5 |
| (29) | 50 | 4 |
|  | 200 | 5 |
|  | 100 | 5 |
| (30) | 50 | 4 |
|  | 200 | 5 |
|  | 100 | 5 |
| (31) | 50 | 5 |
|  | 200 | 5 |
|  | 100 | 5 |
| (32) | 50 | 5 |
|  | 200 | 5 |
|  | 100 | 5 |
| (33) | 50 | 5 |
|  | 200 | 5 |
|  | 100 | 5 |
| (34) | 50 | 5 |
|  | 200 | 5 |
|  | 100 | 5 |
| (35) | 50 | 5 |
|  | 200 | 5 |
|  | 100 | 5 |
| (37) | 50 | 5 |
|  | 200 | 5 |
|  | 100 | 5 |
| (38) | 50 | 4 |
|  | 200 | 5 |
|  | 100 | 5 |
| (39) | 50 | 5 |
|  | 200 | 5 |
|  | 100 | 5 |
| (40) | 50 | 5 |
|  | 200 | 5 |
|  | 100 | 5 |
| (41) | 50 | 4 |
|  | 200 | 5 |
|  | 100 | 5 |
| (42) | 50 | 4 |
|  | 200 | 5 |

TABLE 7-continued

| Compound No. | Concentration of ingredient (ppm) | Control effect |
|---|---|---|
| | 100 | 5 |
| | 50 | 4 |
| (43) | 200 | 5 |
| | 100 | 5 |
| | 50 | 5 |
| (44) | 200 | 5 |
| | 100 | 5 |
| | 50 | 4 |
| (45) | 200 | 5 |
| | 100 | 5 |
| | 50 | 5 |
| (46) | 200 | 5 |
| | 100 | 5 |
| | 50 | 4 |
| (47) | 200 | 5 |
| | 100 | 5 |
| | 50 | 5 |
| (48) | 200 | 5 |
| | 100 | 5 |
| | 50 | 5 |
| (49) | 200 | 5 |
| | 100 | 5 |
| | 50 | 5 |
| (50) | 200 | 5 |
| | 100 | 5 |
| | 50 | 5 |
| A | 500 | 4 |

TEXT EXAMPLE 3

Test for preventive controlling effect on sheath blight (*Rhizoctonia solani*) of rice Rice seeds (var.: Kinki No. 33) were sown in the sandy loam filled in a plastic pot. After raising for 28 days in a greenhouse, the seedlings were subjected to foliage application with a spray liquid of the suspension prepared according to Formulation Example 2 which was diluted with water to the given concentrations. After application, the seedlings were air-dried and then inoculated with mycelia of *Rhizoctonia solani* by spraying an agar suspension containing the fungi. The inoculated seedlings were grown in a dark damp place at 28° C. for 4 days, and the controlling effect was examined. The results are shown in Table 8.

TABLE 8

| Compound No. Present compound | Concentration of active ingredient (ppm) | Control effect |
|---|---|---|
| (2) | 200 | 5 |
| (4) | 200 | 5 |
| (5) | 200 | 5 |
| (6) | 200 | 5 |
| (10) | 200 | 5 |
| (14) | 200 | 5 |
| (18) | 200 | 5 |
| (19) | 200 | 5 |
| (22) | 200 | 5 |
| (30) | 200 | 5 |
| (32) | 200 | 5 |
| (33) | 200 | 5 |
| (34) | 200 | 5 |
| (35) | 200 | 5 |
| (38) | 200 | 5 |
| (40) | 200 | 5 |

TEST EXAMPLE 4

Test for preventive controlling effect on eyespot (*Pseudocercosporella herpotrichoides*) of wheat Wheat seeds (var.: Norin No. 73) were sown in the sandy loam filled in a plastic pot. After raising for 10 days in a greenhouse, the seedlings were subjected to foliage application with a spray liquid of the emulsion prepared according to Formulation Example 4 which was diluted with water to the given concentrations. After application, the seedlings were air-dried and then inoculated with MBC-resistant spores of *Pseudocercosporella herpotrichoides* by spraying a suspension containing the spores. The inoculated seedlings were grown in a dark damp place at 15° C. for 4 days, further incubated for 4 days under illumination, and the controlling effect was examined. The results are shown in Table 9.

TABLE 9

| Compound No. Present compound | Concentration of active ingredient (ppm) | Control effect |
|---|---|---|
| (2) | 500 | 5 |
| (5) | 500 | 5 |
| (6) | 500 | 5 |
| (8) | 500 | 5 |
| (10) | 500 | 5 |
| (12) | 500 | 5 |
| (15) | 500 | 5 |
| (16) | 500 | 5 |
| (18) | 500 | 5 |
| (19) | 500 | 5 |
| (20) | 500 | 5 |
| (21) | 500 | 5 |
| (22) | 500 | 5 |
| (24) | 500 | 5 |
| (25) | 500 | 5 |
| (28) | 500 | 5 |
| (30) | 500 | 5 |
| (31) | 500 | 5 |
| (32) | 500 | 5 |
| (33) | 500 | 5 |
| (34) | 500 | 5 |
| (35) | 500 | 5 |
| (36) | 500 | 5 |
| (44) | 500 | 5 |
| (46) | 500 | 5 |
| (48) | 500 | 5 |
| (49) | 500 | 5 |
| (50) | 500 | 5 |
| B | 500 | 0 |

TEST EXAMPLE 5

Test for curative controlling effect on speckled leaf blotch (*Septoria tritici*) of wheat Wheat seeds (var.: Norin No. 73) were sown in the sandy loam filled in a plastic pot. After raising for 8 days in a greenhouse, the seedlings were inoculated with spores of *Septoria tritici* by spraying a suspension of spores. The inoculated seedlings were grown in a dark damp place at 15° C. for 3 days, and then grown for 4 days under lightening. The seedlings were subjected to foliage application with a spray liquid of the wettable powder prepared according to Formulation Example 1 which was diluted with water to the given concentrations. After application, the seedlings were grown at 15° C. for 11 days under illumination, and the controlling effect was examined. The results are shown in Table 10.

TABLE 10

| Compound No. Present compound | Concentration of active ingredient (ppm) | Control effect |
|---|---|---|
| (1) | 200 | 5 |
| (2) | 200 | 5 |
| (3) | 200 | 5 |
| (5) | 200 | 5 |
| (6) | 200 | 5 |
| (7) | 200 | 5 |
| (8) | 200 | 5 |
| (9) | 200 | 5 |
| (10) | 200 | 5 |
| (11) | 200 | 5 |
| (12) | 200 | 5 |
| (14) | 200 | 5 |
| (15) | 200 | 5 |
| (16) | 200 | 5 |
| (17) | 200 | 5 |
| (18) | 200 | 5 |
| (19) | 200 | 5 |
| (20) | 200 | 5 |
| (21) | 200 | 5 |
| (22) | 200 | 5 |
| (23) | 200 | 5 |
| (24) | 200 | 5 |
| (25) | 200 | 5 |
| (27) | 200 | 5 |
| (28) | 200 | 5 |
| (29) | 200 | 5 |
| (30) | 200 | 5 |
| (32) | 200 | 5 |
| (33) | 200 | 5 |
| (34) | 200 | 5 |
| (38) | 200 | 5 |
| (39) | 200 | 5 |
| (40) | 200 | 5 |
| (41) | 200 | 5 |
| (42) | 200 | 5 |
| (44) | 200 | 5 |
| (45) | 200 | 5 |
| (46) | 200 | 5 |
| (47) | 200 | 5 |
| (48) | 200 | 5 |
| (49) | 200 | 5 |
| (50) | 200 | 5 |
| D | 500 | 0 |

TEST EXAMPLE 6

Test for preventive controlling effect on scab (*Venturia inaequalis*) of apple

Apple seeds (var.: Kohgyoku) were sown in the sandy loam filled in a plastic pot. After raising for 20 days in a greenhouse, the seedlings, with the fourth to fifth foliage leaves open, were subjected to foliage application with a spray liquid of the wettable powder prepared according to Formulation Example 1 which was diluted with water to the give concentrations. After application, the seedlings were air-dried and then inoculated with spores of *Venturia inaequalis* by spraying a suspension containing the spores. The inoculated seedlings were grown in a dark damp place at 15° C. for 4 days, and then grown under illumination for 15 days. The controlling effect was examined. The results are shown in Table 11.

TABLE 11

| Compound No. Present compound | Concentration of active ingredient (ppm) | Control effect |
|---|---|---|
| (4) | 500 | 5 |
| (9) | 500 | 5 |
| (10) | 500 | 5 |
| (12) | 500 | 5 |
| (13) | 500 | 5 |
| (14) | 500 | 5 |
| (20) | 500 | 5 |
| (22) | 500 | 5 |
| (23) | 500 | 5 |
| (24) | 500 | 5 |
| (27) | 500 | 5 |
| (30) | 500 | 5 |
| (32) | 500 | 5 |
| (35) | 500 | 5 |
| (40) | 500 | 5 |
| (43) | 500 | 5 |
| (45) | 500 | 5 |
| (46) | 500 | 5 |
| (49) | 500 | 5 |
| (50) | 500 | 5 |
| C | 500 | 4 |

TEST EXAMPLE 7

Test for preventive controlling effect on anthracnose (*Colletotrichum lagenarium*) of cucumber Cumcumber seeds (var.: Sagami Hanjiro) were sown in the sandy loam filled in a plastic pot. After raising for 14 days in a greenhouse, the seedlings were subjected to foliage application with a spray liquid of the emulsion prepared according to Formulation Example 4 which was diluted with water to the given concentrations. After application, the seedlings were air-dried and then inoculated with spores of *Colletotrichum lagenarium* by spraying a suspension containing the spores. The inoculated seedlings were left to stand in a dark damp place at 23° C. for one day and then were grown under illumination for 4 days. The controlling effect was examined. The results are shown in Table 12.

TABLE 12

| Compound No. Present compound | Concentration of active ingredient (ppm) | Control effect |
|---|---|---|
| (2) | 500 | 5 |
| (3) | 500 | 5 |
| (4) | 500 | 5 |
| (5) | 500 | 5 |
| (6) | 500 | 5 |
| (7) | 500 | 5 |
| (10) | 500 | 5 |
| (12) | 500 | 5 |
| (14) | 500 | 5 |
| (15) | 500 | 5 |
| (16) | 500 | 5 |
| (18) | 500 | 5 |
| (19) | 500 | 5 |
| (20) | 500 | 5 |
| (21) | 500 | 5 |
| (22) | 500 | 5 |
| (24) | 500 | 5 |
| (25) | 500 | 5 |
| (26) | 500 | 5 |
| (27) | 500 | 5 |
| (30) | 500 | 5 |
| (31) | 500 | 5 |
| (32) | 500 | 5 |
| (33) | 500 | 5 |
| (34) | 500 | 5 |
| (38) | 500 | 5 |
| (39) | 500 | 5 |
| (42) | 500 | 5 |
| (43) | 500 | 5 |

TABLE 12-continued

| Compound No. Present compound | Concentration of active ingredient (ppm) | Control effect |
|---|---|---|
| (44) | 500 | 5 |
| (47) | 500 | 5 |
| (49) | 500 | 5 |
| (50) | 500 | 5 |
| C | 500 | 4 |

TEST EXAMPLE 8

Test for curative controlling effect on powdery mildew (*Erysiphe graminis* f. sp. *tritici*) of wheat Wheat seeds (var.: Norin No. 73) were sown in the sandy loam filled in a plastic pot. After raising for 10 days in a greenhouse, the seedlings were inoculated with spores of *Erysiphe graminis* f. sp. *tritici*. The inoculated seedlings were grown at 23° C. for 30 days. The seedlings were subjected to foliage application with a spray liquid of the suspension prepared according to Formulation Example 2 which was diluted with water to the given concentrations. After application, the seedlings were grown in a greenhouse at 23° C. for 7 days, and the controlling effect was examined. The results are shown in Table 13.

TABLE 13

| Compound No. Present compound | Concentration of active ingredient (ppm) | Control effect |
|---|---|---|
| (1) | 500 | 5 |
| (2) | 500 | 5 |
| (3) | 500 | 5 |
| (6) | 500 | 5 |
| (8) | 500 | 5 |
| (11) | 500 | 5 |
| (15) | 500 | 5 |
| (16) | 500 | 5 |
| (18) | 500 | 5 |
| (22) | 500 | 5 |
| (24) | 500 | 5 |
| (25) | 500 | 5 |
| (26) | 500 | 5 |
| (27) | 500 | 5 |
| (31) | 500 | 5 |
| (33) | 500 | 5 |
| (34) | 500 | 5 |
| (36) | 500 | 5 |
| (44) | 500 | 5 |
| (47) | 500 | 5 |
| (49) | 500 | 5 |
| (50) | 500 | 5 |

TEST EXAMPLE 9

Test for preventive controlling effect on gray mold (*Botrytis cinerea*) of cucumber Cucumber seeds (var.: Sagami hanjiro) were sown in the sandy loam filled in a plastic pot. After raising for 14 days in a greenhouse, the seedlings were subjected to foliage application with a spray liquid of the emulsion prepared according to Formulation Example 4 which was diluted with water to the given concentrations. After application, the seedlings were air-dried and then inoculated with mycelia of *Botrytis cinerea* which is resistant to benzimidazole. thiophanate fungicide. The inoculated seedlings were grown in a dark damp place at 15° C. for 3 days, and the controlling effect was examined. The results are shown in Table 14.

TABLE 14

| Compound No. Present compound | Concentration of active ingredient (ppm) | Control effect |
|---|---|---|
| (6) | 500 | 5 |
| (10) | 500 | 5 |
| (12) | 500 | 5 |
| (13) | 500 | 5 |
| (14) | 500 | 5 |
| (16) | 500 | 5 |
| (19) | 500 | 5 |
| (21) | 500 | 5 |
| (24) | 500 | 5 |
| (31) | 500 | 5 |
| (32) | 500 | 5 |
| (33) | 500 | 5 |
| (34) | 500 | 5 |
| (35) | 500 | 5 |
| (36) | 500 | 5 |
| (46) | 500 | 5 |
| (49) | 500 | 5 |
| (50) | 500 | 5 |
| B | 500 | 0 |

TEST EXAMPLE 10

Test for curative controlling effect on leaf rust (*Puccinia recondita*) of wheat Wheat seeds (var.: Norin No. 73) were sown in the sandy loam filled in a plastic pot. After raising for 10 days in a greenhouse, the seedlings were inoculated with spores of *Puccinia recondita*. The inoculated seedlings were left to stand in a dark damp place for one day, and then subjected to foliage application with a spray liquid of the emulsion prepared according to Formulation Example 4 which was diluted with water to the given concentrations. After application, the seedlings were grown under illumination at 23° C. for 7 days. The controlling effect was examined. The test results are shown in Table 15.

TABLE 15

| Compound No. Present compound | Concentration of active ingredient (ppm) | Control effect |
|---|---|---|
| (7) | 500 | 5 |
| (8) | 500 | 5 |
| (11) | 500 | 5 |
| (16) | 500 | 5 |
| (17) | 500 | 5 |
| (19) | 500 | 5 |
| (20) | 500 | 5 |
| (22) | 500 | 5 |
| (24) | 500 | 5 |
| (25) | 500 | 5 |
| (26) | 500 | 5 |
| (27) | 500 | 5 |
| (31) | 500 | 5 |
| (33) | 500 | 5 |
| (34) | 500 | 5 |
| (36) | 500 | 5 |
| (37) | 500 | 5 |
| (41) | 500 | 5 |
| (42) | 500 | 5 |
| (49) | 500 | 5 |
| (50) | 500 | 5 |

What is claimed is:

1. A pyridinylpyrimidine compound of the formula:

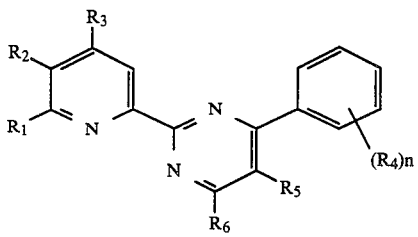

wherein R₁ is lower alkyl; R₂ and R₃ are, the same or different, each hydrogen or methyl; R₄ is, the same or different, each lower alkyl, lower alkoxy, lower haloalkyl or halogen; n is an integer of 0–3; R₅ is hydrogen or lower alkyl and R₆ is hydrogen, lower alkyl, lower alkoxy, lower alkenyloxy or lower alkylthio, or its salt.

2. A pyridinylpyrimidine compound according to claim 1, wherein R₁ is C₁–C₃ alkyl; R₂ and R₃ are, the same or different, each hydrogen or methyl; R₄ is, the same or different, each methyl, ethyl, methoxy, ethoxy, halo(C₁–C₂)alkyl or halogen; n is an integer of 0 to 3; R₅ is hydrogen or methyl and R₆ is hydrogen, methyl, ethyl, methoxy or ethoxy.

3. A pyridinylpyrimidine, compound according to claim 1, wherein R₁ is methyl; R₂ and R₃ are, the same or different, each hydrogen or methyl; R₄ is, the same or different, each methyl, methoxy, fluorine, chlorine or bromine; n is 0, 1 or 2; R₅ is hydrogen, and R₆ is hydrogen, methyl or methoxy.

4. 2-(6-Methyl-2-pyridinyl)-4-phenylpyrimidine or its salt.

5. 4-Methoxy-2-(6-methyl-2-pyridinyl)-6-phenylpyrimidine or its salt.

6. 2-(6-Methyl-2-pyridinyl)-4-o-tolylpyrimidine or its salt.

7. 4-Methoxy-2-(6-methyl-2-pyridinyl)-6-o-tolylpyrimidine or its salt.

8. 4-o-Chlorophenyl-2-(6-methyl-2-pyridinyl)pyrimidine or its salt.

9. 4-o-Chlorophenyl-6-methoxy-2-(6-methyl-2-pyridinyl)pyrimidine or its salt.

10. A fungicidal composition which comprises a pyridinylpyrimidine compound of the formula:

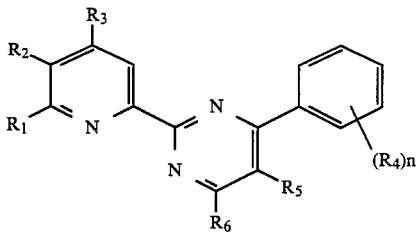

wherein R₁ is lower alkyl; R₂ and R₃ are, the same or different, each hydrogen or methyl; R₄ is, the same or different, each lower alkyl, lower alkoxy, halo(lower)alkyl or halogen; n is an integer of 0 to 3; R₅ is hydrogen or lower alkyl and R₆ is hydrogen, lower alkyl, lower alkoxy, lower alkenyloxy or lower alkylthio, or its salt as an active ingredient, and an inert carrier.

11. A method for controlling fungi which comprises applying a fungicidally effective amount of a pyridinylpyrimidine compound of the formula:

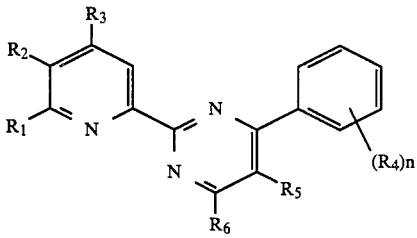

wherein R₁ is lower alkyl; R₂ and R₃ are, the same or different, each hydrogen or methyl; R₄ is, the same or different, each lower alkyl, lower alkoxy, halo(lower)alkyl or halogen; n is an integer of 0 to 3; R₅ is hydrogen or lower alkyl and R₆ is hydrogen, lower alkyl, lower alkoxy, lower alkenyloxy or lower alkylthio, or its salt to fungi.

* * * * *